(12) United States Patent
Towe

(10) Patent No.: US 8,725,270 B2
(45) Date of Patent: May 13, 2014

(54) APPARATUS, SYSTEMS, AND METHODS FOR NEUROSTIMULATION AND NEUROTELEMETRY USING SEMICONDUCTOR DIODE SYSTEMS

(75) Inventor: Bruce C. Towe, Mesa, AZ (US)

(73) Assignee: Arizona Board of Regents, Scottsdale, AZ (US)

( * ) Notice: Subject to any disclaimer, the term of this patent is extended or adjusted under 35 U.S.C. 154(b) by 0 days.

(21) Appl. No.: 13/703,288

(22) PCT Filed: Jun. 8, 2011

(86) PCT No.: PCT/US2011/039642
§ 371 (c)(1),
(2), (4) Date: Feb. 19, 2013

(87) PCT Pub. No.: WO2011/156495
PCT Pub. Date: Dec. 15, 2011

(65) Prior Publication Data
US 2013/0144361 A1   Jun. 6, 2013

Related U.S. Application Data
(60) Provisional application No. 61/352,639, filed on Jun. 8, 2010.

(51) Int. Cl.
*A61N 1/36* (2006.01)
(52) U.S. Cl.
USPC .......................................................... 607/62
(58) Field of Classification Search
USPC .......................................................... 607/62
See application file for complete search history.

(56) References Cited

U.S. PATENT DOCUMENTS

| | | | | |
|---|---|---|---|---|
| 5,579,781 A | * | 12/1996 | Cooke | 600/546 |
| 7,203,548 B2 | * | 4/2007 | Whitehurst et al. | 607/39 |

FOREIGN PATENT DOCUMENTS

| | | |
|---|---|---|
| KR | 20-0391529 | 8/2005 |
| WO | WO 99/06108 | 2/1999 |
| WO | WO 2004/069129 | 8/2004 |
| WO | WO 2005/120203 | 12/2005 |

OTHER PUBLICATIONS

Heetderks. *IEEE Transactions on Biomedical Engineering*. 35(5):323, 1988.
International Preliminary Report on Patentability in PCT/US2011/039642 issued Dec. 10, 2012.
Matthaei, *IRE Transactions on Microwave Theory Tech*. M11-10: 23-28, 1961.
Mohseni, et al., *IEEE Transactions on Neural Systems and Rehabilitation Engineering*. 13(3), 2005.
Sard, et al., *IEEE Trans Mico Theory Techvol*. 14: 608-618, 1966.
Towe. *IEEE Transactions on Biomedical Engineering*. BME-33(10), 1986.
Wise, et al., *Proceedings of the IEEE*. 92(1), 2004.

\* cited by examiner

*Primary Examiner* — George Manuel
(74) *Attorney, Agent, or Firm* — Fulbright & Jaworski LLP

(57) ABSTRACT

Methods and systems for neurostimulation and/or neurotelemetry of electrically-excitable biological tissue. In one embodiment, a method includes providing a radio frequency output to a diode implanted in biological tissue. The radio frequency output cause current to flow in the diode that is sufficient to provide neurostimulation. Additionally, a radio frequency receiver is configured to receive a second harmonic signal from the diode, which can be used to control the radio frequency output.

25 Claims, 5 Drawing Sheets

APPARATUS, SYSTEMS, AND METHODS FOR NEUROSTIMULATION AND NEUROTELEMETRY USING SEMICONDUCTOR DIODE SYSTEMS

This application is a national phase application under 35 U.S.C. §371 of International Application No. PCT/US2011/039642 filed Jun. 8, 2011, which claims the benefit of priority to U.S. Provisional Patent Application Ser. No. 61/352,639, filed Jun. 8, 2010, the disclosures of which are hereby incorporated by reference in their entirety.

BACKGROUND

1. Technical Field

This invention relates to methods of neurotelemetry from human body tissue through the use of implantable semiconductor diode devices.

2. Description of Related Art

There is interest in methods of directly stimulating bioelectrically excitable tissues by artificial means since this allows their function to be evoked or modified, thus providing a therapeutic or otherwise desirable biological effect. For example, neurostimulation may be used for restoring function in cases of neural injury or disease. Neurostimulation in this context refers to the stimulation of electrically excitable tissues of living things. This can include, for example, the human tissues of the brain, heart, muscle, and nervous system.

There is also interest in recording tissue bioelectrical events. Tissue bioelectrical events arise from the flow of ionic currents as a result of the action of cellular ionic pumps and channels, which underlie the bioelectrical activity of neural and muscle tissues in the body. These neural and muscle tissues are associated with the function of the brain, muscles, and nervous system. The ionic currents are well known and are used for electrocardiograms, electroneurograms, and electromyograms.

A common method of neurostimulation is the application of pulsed electrical currents directly to tissue through electrodes implanted within tissue or indirectly through the body surface.

Electrical currents applied to tissue are known to affect the membranes of excitable cells, causing a depolarizing effect that can lead to a cell action event that depends on its type and biological function. The pulsing of currents is needed to prevent accommodation to current flows and to fulfill certain physiologic conditions that enables electricity to be effective.

It is also possible to apply electrical currents to the body surface in which case they diffuse in the volume conductivity of tissue and attenuate according to well known laws. These currents can also stimulate near-surface nerves and muscle tissues to some degree, but cannot reach deeper tissues because of high electrical losses in tissue and the rise in the needed current levels to above those that would cause electrical shock.

The strong diffusion of electrical current in tissues from surface electrodes means that specific stimulation of a given nerve or nerve fiber within a bundle is very difficult and rather there is a tendency for electrical currents applied to the body surface to broadly stimulate in undesirable ways. Implantable electrodes overcome these problems but are invasive and suffer from the undesirable need to either run wires through the skin or work with relatively bulky implanted power systems that run on batteries or are powered by external radiofrequency (RF) powering techniques.

Technologies that deliver electrical currents to tissues by way of RF induction to an implanted device are well known to the art. In general these approaches use an inductor implanted within the body to magnetically couple to an external RF field. Often times this inductor is coupled with a capacitor to form a resonant circuit that is more efficient in coupling to applied RF energy. These devices are relatively large and can be on the order of a centimeter in size. A discussion of methods of coupling energy to implanted RF devices was published by Heetderks (1988) and an overview of the current state of the art and sizes of neuroimplants by Wise et al. (2004) and by others is incorporated herein by reference. The Heetderks paper mostly confines itself to power induction at frequencies below about 50 MHz.

High frequency currents are not known to stimulate bioelectrically excitable tissues of the nervous system of the body because they are faster than physiologic events can respond. As long as they are relatively high frequency, above several tens of kilohertz and continuing up into the megahertz region currents do not stimulate bioelectrical events or sensations of pain.

A major concern in the development of neurostimulators for implantation near nerve or muscle for therapeutic applications in the human body is the size of the implant. It is preferable that the implanted devices be small and perhaps something that could be introduced into the body through minimally invasive methods, such as syringe needle injection. This is not only for ease of insertion into tissues, but so that they produce less complications such as pressure or force against sensitive tissues as a person moves or exercises. There is also less immunological response and inflammation of tissues with small devices as it reduces their attendant risk of complications. This feature tends to encourage more widespread use in situations which are elective rather than critical.

A neurostimulation device known as a Bion™ has been described by Loeb et al. which is an example of present methods of designing implantable neurostimulation devices. It is a small cylindrical electrical device which derives its energy from an externally applied RF field. As presently designed, the size of these devices ranges from 6 mm to about 1.5 cm. These devices incorporate active LSI logic and inductive RF powering.

Some versions store energy in batteries or capacitors to deliver later upon digital command and so provide electrical pulses through integral electrodes to neural tissues. These devices are targeted for therapeutic stimulation of muscle and nerves by being implanted within body tissues and in some cases are used for pain relief, treating urinary incontinence, and can be programmed to actuate nerves and muscles in the restoration of lost function in limbs. A disadvantage of these devices is their relative complexity and large size. The large size limits their medical applicability to situations where they can be introduced by surgery or through a large trocar.

This application incorporates by reference provisional patent application No. 61/180,549 filed May 22, 2009, and Patent Cooperation Treaty application number PCT/US2010/035753, filed May 21, 2010, each entitled "Apparatus, Systems, and Methods for Neurostimulation and Neurotelemetry Using Semiconductor Diode Systems."

SUMMARY

A method of providing neurostimulation is presented. In one embodiment, the method includes providing a radio frequency transmitter proximal to tissue overlying a diode implanted in biological tissue, where the radio frequency transmitter is configured to emit a radio frequency output.

The method may also include creating a current flow from the diode, where the current flow is sufficient to provide neurostimulation of the biological tissue. In one embodiment, the method includes providing a radio frequency receiver, where the radio frequency receiver is configured to receive a second harmonic signal from the diode.

In some embodiments, the method includes adjusting the radio frequency output in response to the received second harmonic signal. The amplitude of the radio frequency output may be adjusted in response to the received second harmonic signal. Additionally, the frequency of the radio frequency output may be adjusted in response to the received second harmonic signal.

In some embodiments, a signal is outputted in response to the received second harmonic signal. In some embodiments, the biological tissue where the diode is implanted may include brain tissue, muscle tissue, or nervous system tissue. Additionally, the diode may be arranged in a bridge configuration with additional diodes.

In some embodiments, the diode is a semiconductor diode. The diode may also be connected to at least one conductor that forms an antenna. In some embodiments, each electrode of the diode is connected to a conductor, forming a dipole antenna. The conductors may also serve to attach, physically and electrically, the diode to the biological tissue. In some embodiments, the diode is configured to rectify the radio frequency output from the radio frequency transmitter.

An apparatus for neurostimulation is also presented. In one embodiment, the apparatus includes a radio frequency transmitter configured to emit a radio frequency output and excite a diode implanted in biological tissue. The apparatus may also include a radio frequency receiver configured to receive a second harmonic signal from the implanted diode, where the radio frequency receiver is further configured to report the intensity of the received second harmonic signal emitting from the radio frequency transmitter to the diode.

In one embodiment, the radio frequency receiver is configured to report the intensity of the second harmonic signal to a display. The radio frequency receiver may be configured to report the intensity of the second harmonic signal to a feedback controller, where the feedback controller is configured to adjust the power of the emitted radio frequency output in response to the reported intensity of the second harmonic signal.

In one embodiment the diode is a semiconductor diode. The diode may also be connected to at least one conductor that forms an antenna. In some embodiments, each electrode of the diode is connected to a conductor, forming a dipole antenna. The conductors may also serve to attach, physically and electrically, the diode to the biological tissue.

In some embodiments, the radio frequency transmitter may be configured to emit radio waves in the microwave frequency range, which may range from 300 MHz to 300 GHz. The radio frequency transmitter may be configured to emit radio waves at a frequency between 1 KHz to 10 GHz. The radio frequency output may be modulated so that it is pulsed for a time period between 10 microseconds and 10 milliseconds and so that it is pulsed 1 to 1000 times per second as determined by the requirements of the neurostimulation.

A method for determining a current flow used for neurostimulation is also presented. In some embodiments, the method includes providing a radio frequency transmitter proximal to tissue overlying a diode implanted in biological tissue, where the radio frequency transmitter is configured to emit a radio frequency output. The method may include emitting a first output from the radio frequency transmitter and creating a first current flow in the diode. The method may include receiving a first received harmonic signal from the diode as a result of the first current flow using a radio frequency receiver. Additionally, the method may include emitting a second output from the radio frequency transmitter and creating a second current flow in the diode. In some embodiments, the method may include receiving a second received harmonic signal from the diode as a result from the second current flow using a radio frequency receiver and calculating the relationship between output from the radio frequency transmitter and current flow in the diode. In some embodiments, the first output and the second output from the radio frequency transmitter comprise pulses of different amplitudes. Also, in some embodiments, calculating the relationship between the output from the radio frequency transmitter and the current flow in the diode may include computing a first ratio of the first output from the radio frequency transmitter to the first received harmonic signal from the diode, computing a second ratio of the second output from the radio frequency transmitter to the second received harmonic signal from the diode, and using the difference between the first ratio and the second ratio to determine the amount of current flow in the diode for a range of outputs from the radio transmitter.

The term "coupled" is defined as connected, although not necessarily directly, and not necessarily mechanically. The terms "a" and "an" are defined as one or more unless this disclosure explicitly requires otherwise. The terms "substantially," "approximately," "about," and variations thereof are defined as being largely but not necessarily wholly what is specified, as understood by a person of ordinary skill in the art. In one non-limiting embodiment, the term substantially refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but it may also be configured in ways other than those specifically described herein.

DETAILED DESCRIPTION OF EXEMPLARY EMBODIMENTS

Various features and advantageous details are explained more fully with reference to the nonlimiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

Figure 1:
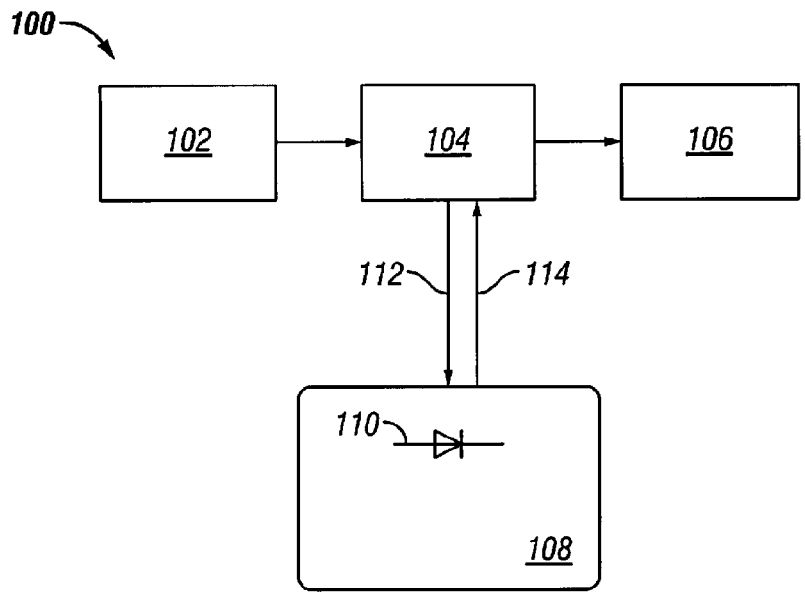
FIG. 1 is a schematic block diagram showing a neurostimulation system.

FIG. 1 illustrates one embodiment of a system 100 for neurostimulation. A radio frequency transmitter 102 is coupled to a diplexer 104 that is configured to emit a radio frequency output. The diplexer 104 may act as an antenna. The diplexer output is a radio frequency output 112, which is controlled by the radio frequency transmitter 102. The output may be controlled in frequency, amplitude (intensity) and/or modulation. For example, the radio frequency transmitter 102 may be configured to emit a radio frequency output 112 in the microwave frequency range. In some embodiments, the radio frequency output 112 may be between 1 KHz to 10 GHz. The radio frequency energy emitted must be substantially spectrally pure and so must employ filtering to insure that the second and higher order harmonics are suppressed at least 80 db below the transmitted signal and preferably 100 db. This is achieved typically by the use of good engineering design of the power amplifier stages and through the use of passive low-pass filters known to the art. Furthermore, the radio frequency output 112 may be modulated. In one embodiment, it is pulsed for a time period between 10 microseconds and 10 milliseconds and so that it is pulsed 1 to 1000 times per second.

The radio frequency output 112 is directed toward a diode 110 implanted in biological tissue 108. For example, the diode 110 may be a semiconductor diode and may be implanted in a human brain. The radio frequency output 112 can cause current to flow in the diode 110. The diode 110 is connected to biological tissue and the current from the diode 110 causes neurostimulation. In some embodiments, the diode acts as a rectifier of the radio frequency output 112. As the radio frequency output 112 is rectified a second harmonic signal 114 is produced and may be emitted. The second harmonic signal 114 will have approximately twice the frequency of the radio frequency output 112. In some embodiments, additional diodes may be used and/or additional harmonics may be produced. For example additional diodes may be used to form a full wave rectifier.

The nonlinear current-voltage behavior of semiconductor diodes may create a higher-order harmonic in response to an applied alternating current. The magnitude of the amplitudes of the second and higher order harmonics carry information about the instantaneous current amplitude through the diode. Thus, in response to driven currents from a nearby radio frequency transmitter, the second and higher-order harmonics of the driving frequency may emit from the diode. Although this embodiment describes using the second-order harmonic, some embodiments may use higher-order harmonics.

The second harmonic signal 114 may emit from the diode 110 and leave the biological tissue 108. In some embodiments, the diplexer 104 may be configured to receive the second harmonic signal 114. The diplexer 104 may be coupled to a radio frequency receiver 106, which can receive the second harmonic signal 114. In some embodiments, the radio frequency receiver 106 may use an antenna that is not shared with the radio frequency transmitter 102. For example, in one embodiment a radio frequency transmitter 102 may be placed on a patient's chest and the radio frequency receiver 106 may be placed on the patient's back, each with its own antenna.

The radio frequency receiver 106 may be configured to measure the second harmonic signal 114. Additionally, the radio frequency receiver 106 may simultaneously or sequentially measure higher harmonics, including the third through fifth harmonic, although harmonics higher than the third are typically attenuated. The receiver may measure the frequency, amplitude, and may demodulate the second harmonic signal 114, as well as higher order harmonics. The real-time demodulated envelope of the second harmonic or that any of the higher order harmonics may closely resemble the diode current waveform as conducted to tissue. Thus, the receiver may display a waveform that corresponds to the instantaneous current in the diode, which corresponds to the amount of neurostimulation. Because of potential non-linear responses between the received harmonic signal and the induced current, the system may be calibrated to correct for the nonlinearities. In some embodiments, the radio frequency receiver 106 is further configured to report the intensity of the received second harmonic signal 114. The radio frequency receiver 106 may report the intensity of the signal through a display. For example, the radio frequency receiver 106 may have a digital liquid crystal display configured to display a numeric readout of the intensity of the second harmonic signal 114. Additionally, the radio frequency receiver 106 may be configured to report the intensity of the second harmonic signal 114 to a computer that can log, display or retransmit the received signal. For example, radio frequency receiver 106 may send the measured intensity to a remote server configured to store medical records.

The radio frequency receiver 106 may need to differentiate different signals received by the diplexer. For example, the signal received by the radio frequency receiver 106 may be a combination of radio frequency output 112 and second harmonic signal 114. Especially when a common antenna is used, both signals may be present at the input of the radio frequency receiver. In some embodiments, different antennas may be used for the radio frequency transmitter 102 and the radio frequency receiver 106 such that the input signal at the radio frequency receiver 106 is substantially free of radio frequency output 112. However, in the case where the both signals are present, the radio frequency receiver 106 may separate the received signals. In one embodiment, the radio frequency receiver may use analog components, such as passive components and operational amplifiers, to filter the received signal by frequency. Because the second harmonic signal 114 has twice the frequency of the radio frequency output, analog filters may work well to separate the signals. Additionally, if higher-order harmonics are used, the harmonic frequency will be higher (and farther from the radio frequency output on a frequency spectrum) which would increase the efficacy of analog filters. Once separated, the radio frequency receiver may determine the amplitude of the second harmonic signal 114. In other embodiments, the received signal in the radio frequency receiver may be digitized. In this example, a Fast Fourier Transform may be used to separate the received signals and determine the amplitude of the received second harmonic signal 114.

Detection of the second harmonic signal 114 may be used for several purposes. For example, the lack of a second harmonic signal 114 may indicate that the diode 110 is not functional, not where it should be, or is not making proper contact with the biological tissue 108. The presence and shape of the second harmonic signal 114 may indicate the proper functioning/positioning of the diode. In a basic implementation, the strength of the second harmonic signal 114 may be used to optimize the position of the radio frequency transmitter 102 to obtain a desired coupling between the radio frequency transmitter 102 and the diode 110.

Figure 2:
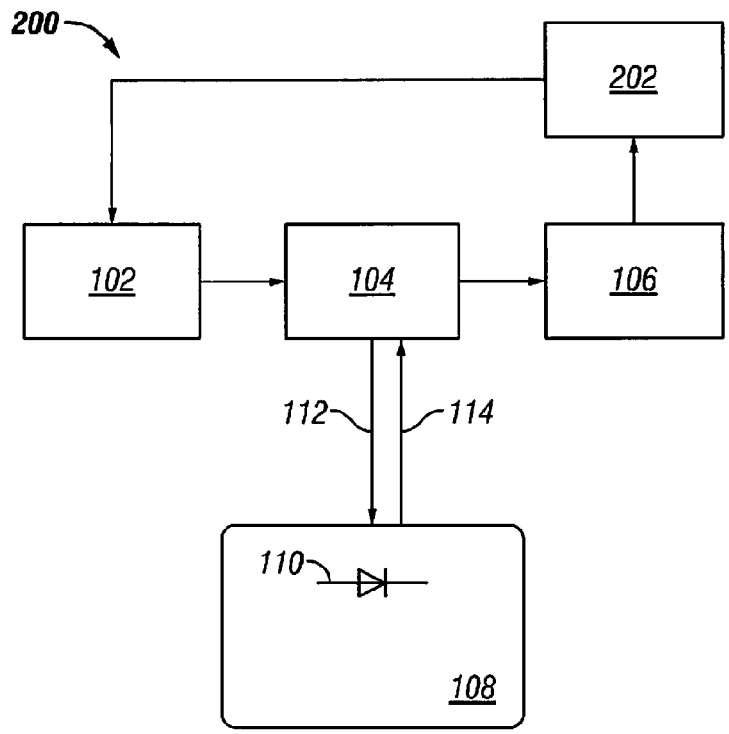
FIG. 2 is a schematic block diagram showing a neurostimulation system with a feedback control loop.

FIG. 2 shows one embodiment of a neurostimulation system 200. The system 200 has a radio frequency transmitter 102, a diplexer 104, a radio frequency output 112, an implanted diode 110, a second harmonic signal 114, and a radio frequency receiver 106, as described above. Additionally, the neurostimulation system 200 has a feedback controller 202. The feedback controller 202 is configured to receive a signal from the radio frequency receiver 106. In one embodiment, the feedback controller 202 may receive a signal that represents the intensity of the measured second harmonic signal 114. The signal received by the feedback controller 202 may be a digital or analog signal.

The feedback controller 202 may then control the radio frequency transmitter 102. In one embodiment, the feedback controller 202 may cause the radio frequency transmitter 102 to raise or lower the intensity of the radio frequency output 112 until the signal received by the feedback controller 202 from the radio frequency receiver 106 reaches a particular value. In some embodiments, the particular value may be adjusted by a patient and/or doctor. For example, a doctor may prescribe a certain amount of neurostimulation, enter that number into the feedback controller 202, and the system 200 would then adjust the radio frequency output 102 until a desired amount of neurostimulation is achieved, as evidenced by the intensity of the second harmonic signal 114. Other characteristics of the radio frequency output 112 may also be adjusted in response to the received second harmonic signal 114. For example, the frequency or modulation of the radio frequency output 112 may be adjusted to achieve a desired amount or type of neurostimulation.

Figure 3:
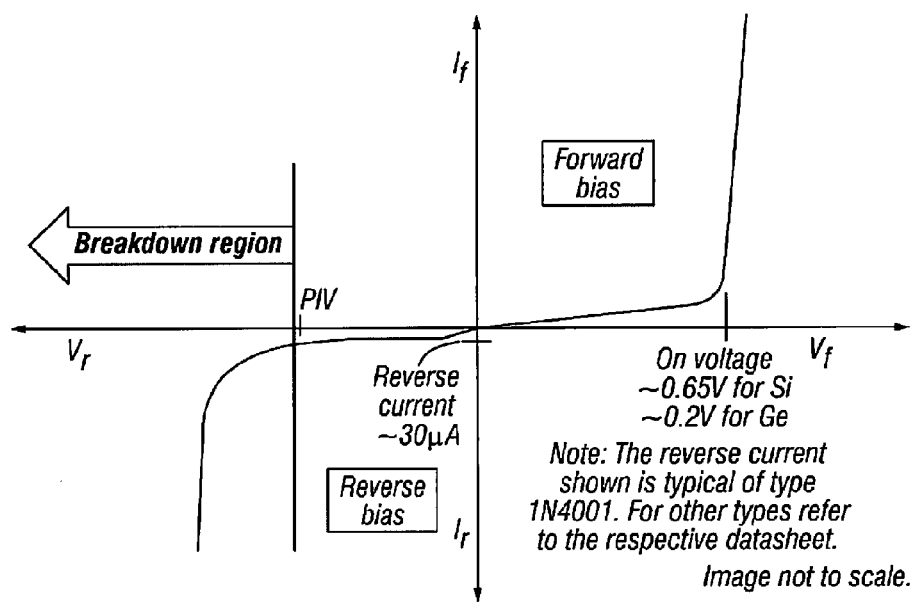
FIG. 3 is a graph showing the relationship between current and voltage in a diode.

FIG. 3 is a graph showing the relationship between voltage and current in one embodiment of diode 110. As, voltage across the diode 110 increases, the current increases. After the voltage reaches a threshold (labeled ON voltage), the current begins to increase much faster as voltage continues to increase. It is this relationship between voltage and current that causes a diode 110 to rectify the incoming signal. For example, the radio frequency output 112 may cause a sinusoidal wave to be applied to the leads of the diode 110. As the voltage is negative (but above the breakdown region) and/or positive (and below the ON voltage), the output current of the diode will be close to zero. However, as the voltage across the diode increases above the ON voltage, current will flow through the diode.

Figure 4A:
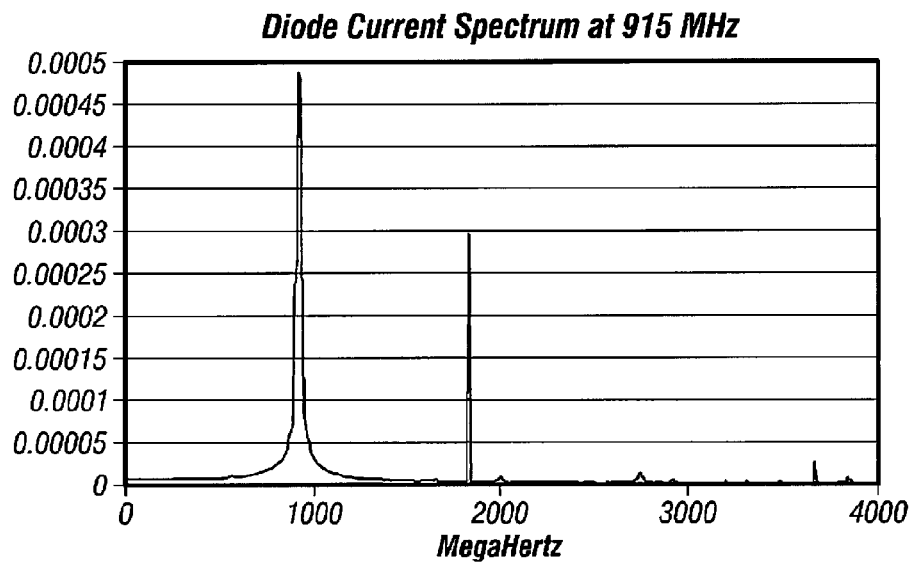
FIG. 4A is graph showing a graph showing the frequency response of a neurostimulation system.

FIG. 4A is a graph showing the frequency response of a system 100 as modeled in PSPICE. In this example, the radio frequency output 112 is operated at 915 MHz, and is shown by the large peak on the left. The second harmonic signal 114 is shown by the smaller peak on the right. The second harmonic signal 114 has a frequency of 1830 MHz. Higher order harmonics are also shown in FIG. 4A, and one can see how the amplitude decreases as the order of the harmonic increases. Although the amplitude of these harmonics may be smaller, these harmonics may still be useful to monitor the implanted diode.

Semiconductor junction diodes have nonlinear current-voltage transfer characteristics. The Shockley equation (Eq. 1) shows the relationship of diode forward current to an applied bias voltage.

$$I = I_S(e^{V_D/(nV_T)} - 1) \qquad \text{Eq. 1}$$

where I is the diode current, $I_S$ is a scale factor called the saturation current, $V_D$ is the voltage across the diode, $V_T$ is the thermal voltage, and n is the emission coefficient.

Figure 4B:
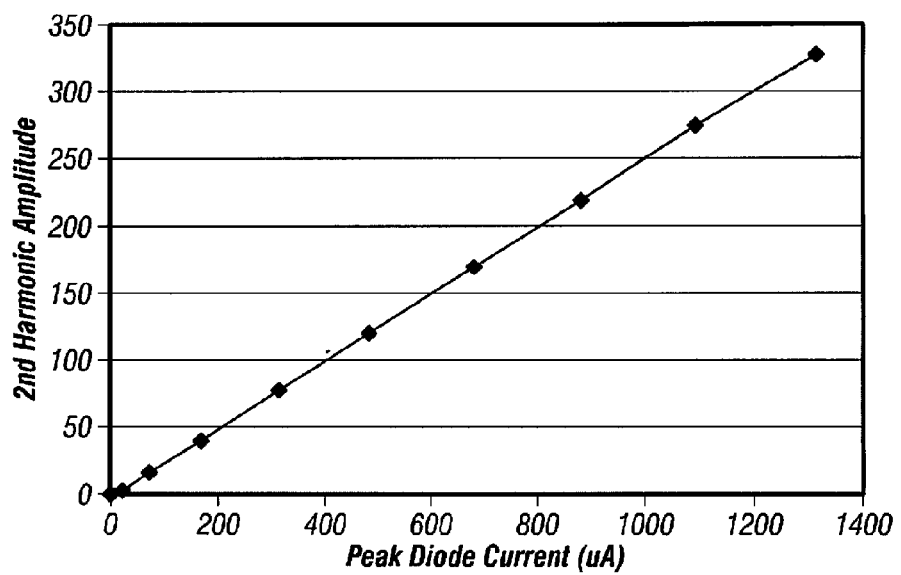
FIG. 4B is a graph of the second harmonic amplitude (1830 MHz) for a 915 MHz current flow through a Skyworks Inc CDF-7631 Schottky diode versus the current through the diode.

The diode current waveform is therefore nonlinear with the radio frequency voltage induced by a remote transmitter across the implanted diode. The resulting current flow nonlinearity generates harmonics of the driving frequency. For example, if a 915 MHz microwave radiation is applied to the diode, the current flow through the diode will be rectified and have a significant frequency component at 1830 MHz. The current flow in tissue resulting from this harmonic generation process causes the radiation of it as a signal which can be detected outside of the body. The magnitude of this harmonic frequency component is linearly proportional to the rectified tissue current flow. Thus, changes in the harmonic amplitude may directly reflect tissue neurostimulation current changes. FIG. 4B is a PSPICE simulation of this diode behavior whereby the diode is driven by a variable voltage source at 915 MHz and the envelope of the 1830 MHz current flow through the diode is shown on the y-axis. A linear relationship over a wide current range is observed.

Thus, by demodulating the envelope of the second harmonic radio frequency signal emitting from tissue it is possible to record and display changes in the neurostimulation current. The second harmonic signal is easily detected wirelessly by a conventional radio receiver tuned to its frequency. Because the second harmonic reflects the instantaneous current flow through the diode, demodulating the received envelope of the second harmonic reconstructs the real-time electrode current pulse and shows features of the current pulse such as its rise, sustain, and fall times. These are potentially interesting and useful in monitoring implant functionality, changes in electrode behavior over time, and assessing tissue responses to the implant such as changes in electrode impedances with its progressive tissue encapsulation over the healing interval after implantation.

Real-time recording of neurostimulation current through second-harmonic reception and demodulation is useful because it gives important insight into changes caused by undesirable motion of the external radio frequency exciter antenna. This approach to monitoring implant current flow, however, may give only a relative indication of the time-varying implant current delivery. It would be desirable in some applications to have an actual calibration reference so as to be able to track current flow in absolute units of current.

This can be accomplished by taking advantage of the nonlinear slope of the diode i-v curve near its turn-on threshold. Since the second harmonic of the driven current flow is proportional to the diode peak current it is possible to determine the actual magnitude of the current flow by applying a ramp, or stairstep, of radio frequency drive level and then monitor the resulting increase in second harmonic demodulated envelope.

The amplitude of the current, which increases with a drive voltage ($V_d$ in Eq. 1), is an exponentially increasing function. Because $V_t$ is known (a function of the diode manufacture), the measurement of the slope between two successively driven amplitudes of radio frequency gives an indentifying characteristic as to where a given drive voltage falls on the diode i-v curve. Thus measurement of the ratio of second harmonic amplitude change relative to a known ratio of change of two successive radio frequency drive amplitudes gives sufficient information to establish where the first and second amplitudes of the current operating point fall on the i-v curve. Thus the true current that the implant drives in tissue can be determined by calculation or by using a lookup table. This approach has the advantage of giving a current value that can be absolutely determined since it does not depend solely on the amplitude of the second harmonic but looks at its rate of change as an identifier of the i-v operating point for a given radio frequency drive level applied.

Figure 4C:
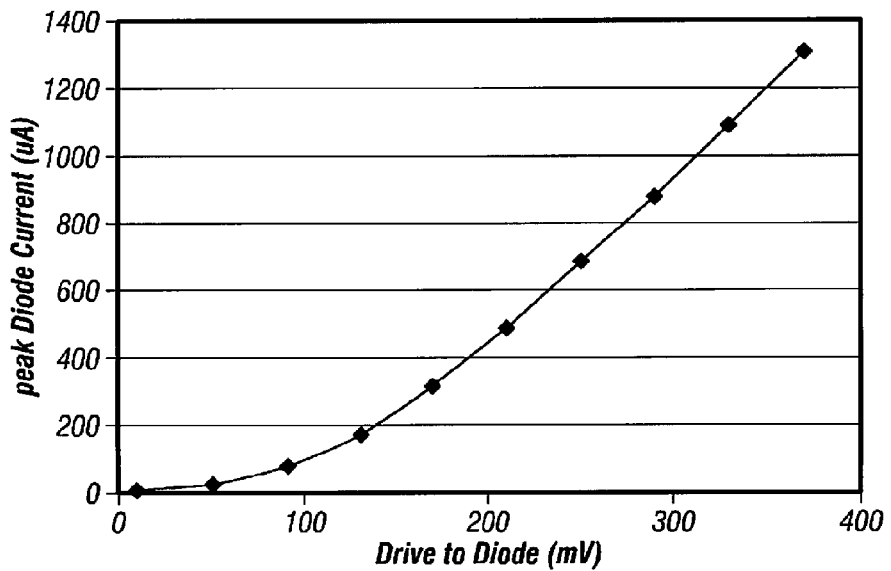
FIG. 4C is a graph showing the nominal i-v characteristic of a diode showing the nonlinear response of the current to the applied voltage.
Figure 4D:
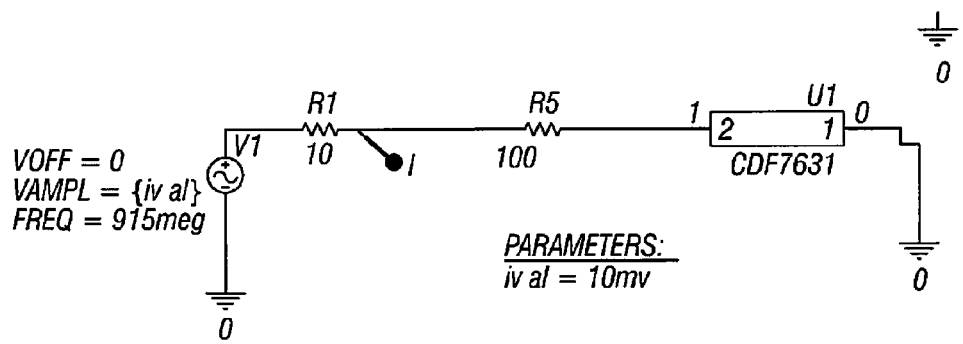
FIG. 4D is a schematic drawing of a PSPICE circuit used to obtain the data in FIG. 4B.

FIG. 4C shows this relationship derived from the PSPICE model shown FIG. 4D. PSPICE is an electronic circuit modeling software package. For a stairstep of radio frequency drive voltages applied at 915 MHz and for a Skyworks CDF-7631 diode, the amplitude of the second harmonic of the diode current shows a characteristic exponential curve. Thus, for example, measuring the percent change in the second harmonic amplitude for two radio frequency amplitude drive levels will calculate a numerical value that uniquely identifies the specific current level on the known characteristics of the diode's i-v curve.

The process of using a radio frequency amplitude change to determine what radio frequency level constitutes a particular current flow in the diode may be used to calibrate the system. The calibration can occur before every use of the neurostimulator or at predetermined intervals, such as after daily application of the external drive device. The measurement can be made using a series of pulses less than about 50 microseconds in duration so as to be sufficiently short that they will not evoke a significant neurostimulation event. In order to ensure sufficiently good signal to noise ratio in the received second harmonic signal so as to make the signal amplitude measurement with sufficient precision, signal processing, such as averaging of multiple events, can be used.

Figure 5:
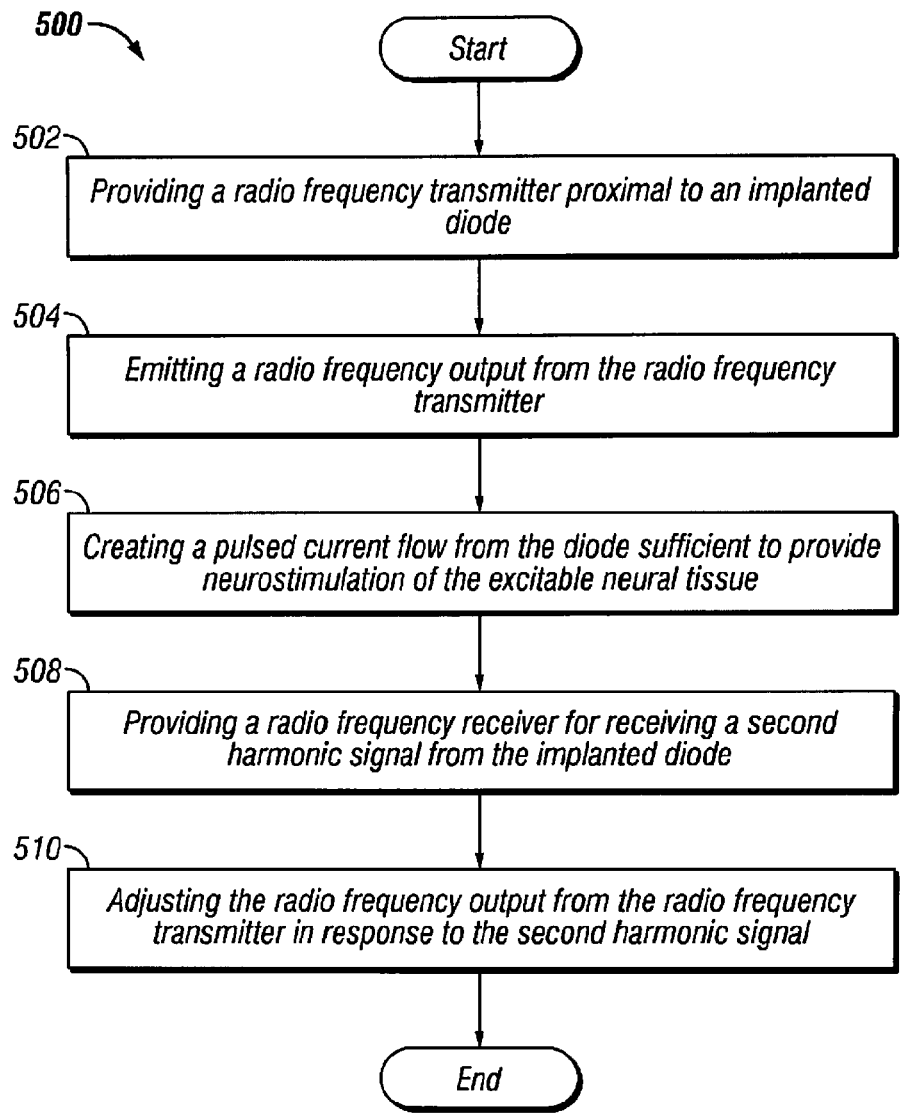
FIG. 5 is a schematic flow chart showing one embodiment of a method for neurostimulation.

Referring now to FIG. 5, the schematic flow chart diagram is generally set forth as a logical flow chart diagram. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

FIG. 5 illustrates one embodiment of a method 500 for providing neurostimulation. In one embodiment, the method 500 starts by providing 502 a radio frequency transmitter proximal to an implanted diode. The transmitter may be placed proximal to the implanted diode in order to increase the transmission of energy from the radio frequency transmitter to the diode. Next the method continues to emitting 504 a radio frequency output from the radio frequency transmitter. The output frequency then creates 506 a pulsed current flow from the diode sufficient to provide neurostimulation of the biological tissue. In some embodiments, the current flow may not be pulsed, and may resemble a DC current, depending on the type of diode or diodes used.

Method 500 continues by providing 508 a radio frequency receiver for receiving a second harmonic signal from the implanted diode. The second harmonic signal may be produced by the implanted diode as the diode rectifies the radio frequency output from the radio frequency transmitter. The method 500 continues to step 510 of adjusting the radio frequency output from the radio frequency transmitter in response to the second harmonic signal. This step may be the step that "closes the loop." By providing feedback in the form of the second harmonic signal, the system is able to control the intensity, frequency, or modulation of the radio frequency output to adjust the amount of current or the waveform used for neurostimulation.

Likewise, the second harmonic amplitude from method 500 can be used as input to a method of determining diode current values. This method consists of the steps of applying a sequence of two or more radio frequency pulses of a duration in the range of 10 microseconds to 50 microseconds separated by an interval of 50 microseconds to 10 milliseconds to the implanted diode. The resulting pulsed second harmonic amplitude detected by method 500 for each of the two radio frequency pulses applied is then recorded. A calculation is performed using a microcomputer or similar system that ratios the second harmonic amplitude responses and then uses the result to determine a current value in the implant based on the use of a look-up table. The look-up table is constructed using manufacturer information of the i-v diode characteristics. The look-up table may also be generated using empirical data that corresponds to the received signal and the measured current in the diode. This empirical data may be obtained in simulated tissue or in patients.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

1. Heetderks, W. "RF Powering Of Millimeter- and Submillimeter-Sized Neural Prosthetic Implants" IEEE Transactions on Biomedical Engineering, Vol. 35, No. 5, 323. May 1988.
2. K. D. Wise, D. J. Anderson, J. F. Hetke, D. R. Kipke, K. Najafi, Wireless Implantable Microsystems: High-Density Electronic Interfaces To The Nervous System Proceedings Of The Ieee, Vol. 92, No. 1, January 2004

3. P. Mohseni, K. Najafi, S. J. Eliades, And X. Wang, "Wireless Multichannel Biopotential Recording Using An Integrated Fm Telemetry Circuit", Ieee Ieee Transactions On Neural Systems And Rehabilitation Engineering, Vol. 13, No. 3, September 2005

4 G. L. Matthaei, "A Study of the Optimum Design of Wide-Band Parametric Amplifiers and Up converters Up Converters", IRE Transactions on Microwave Theory Tech. Vol. MTT-10, pp. 23-28 Jan. 1961.

5. E. Sard, B. Peyton, S. Okwit, "A positive resistance up-converter for ultra-low noise amplification" IEEEE Trans. Micro Theory Techvol. 14, pp. 608-618, December 1966.

6. Towe, B. C., "Passive Biotelemetry by Frequency Keying", IEEE Transactions on Biomedical Engineering, vol. BME-33, no. 10, October 1986.

7. J. Patrick Reilly, Applied Bioelectricity: From Electrostimulation to Electropathology, Springer Verlag, New York, 1998.

What is claimed is:

1. A method of providing neurostimulation, the method comprising:
providing a radio frequency transmitter proximal to tissue overlying a diode implanted in biological tissue, where the radio frequency transmitter is configured to emit a radio frequency output;
creating a current flow from the diode, where the current flow is sufficient to provide neurostimulation of the biological tissue; and
providing a radio frequency receiver, where the radio frequency receiver is configured to receive a harmonic signal from the diode.

2. The method of claim 1, further comprising adjusting the radio frequency output in response to the received harmonic signal.

3. The method of claim 2, where the amplitude of the radio frequency output is adjusted in response to the received harmonic signal.

4. The method of claim 2, where the frequency of the radio frequency output is adjusted in response to the received second harmonic signal.

5. The method of claim 1, further comprising outputting a signal in response to the received harmonic signal.

6. The method of claim 1, where the biological tissue comprises brain tissue, muscle tissue, or nervous system tissue.

7. The method of claim 1, where the diode is a semiconductor diode.

8. The method of claim 1, where the diode is connected to at least one conductor that forms an antenna.

9. The method of claim 1, where the radio frequency transmitter is configured to emit radio waves in the microwave frequency range.

10. The method of claim 1, where radio frequency transmitter is configured to emit radio waves at a frequency between 1 KHz to 10 GHz.

11. The method of claim 1, where the radio frequency output is modulated so that it is pulsed for a time period between 100 microseconds and 10 milliseconds and so that it is pulsed in the range of 1 to 200 pulses per second.

12. The method of claim 1, where the diode is configured to rectify the radio frequency output from the radio frequency transmitter.

13. The method of claim 1, where the diode is arranged in a bridge configuration with additional diodes.

14. An apparatus for providing neurostimulation, comprising:
a radio frequency transmitter configured to emit a radio frequency output and excite a diode implanted in biological tissue; and
a radio frequency receiver configured to receive a harmonic signal from the implanted diode, where the radio frequency receiver is further configured to report the intensity of the received harmonic signal.

15. The apparatus of claim 14, where the radio frequency receiver is configured to report the intensity of the harmonic signal to a display.

16. The apparatus of claim 15, where the radio frequency receiver is configured to report the intensity of the harmonic signal to a feedback controller, where the feedback controller is configured to adjust the power of the emitted radio frequency output in response to the reported intensity of the harmonic signal.

17. The apparatus of claim 14, where the biological tissue comprises brain tissue, muscle tissue, or nervous system tissue.

18. The apparatus of claim 14, where the diode is a semiconductor diode.

19. The apparatus of claim 14, where the diode is connected to at least one conductor that forms an antenna.

20. The apparatus of claim 14 where radio frequency transmitter is configured to emit radio waves in the microwave frequency range.

21. The apparatus of claim 14 where radio frequency transmitter is configured to emit radio waves at a frequency between 1 KHz to 10 GHz.

22. The apparatus of claim 14 where the radio frequency output is modulated so that it is pulsed for a time period between 10 microseconds and 10 milliseconds and so that it is pulsed 1 to 1000 times per second.

23. A method for determining a current flow used for neurostimulation comprising:
providing a radio frequency transmitter proximal to tissue overlying a diode implanted in biological tissue, where the radio frequency transmitter is configured to emit a radio frequency output;
emitting a first output from the radio frequency transmitter;
creating a first current flow in the diode;
receiving a first received harmonic signal from the diode as a result of the first current flow using a radio frequency receiver;
emitting a second output from the radio frequency transmitter;
creating a second current flow in the diode;
receiving a second received harmonic signal from the diode as a result from the second current flow using a radio frequency receiver; and
calculating the relationship between output from the radio frequency transmitter and current flow in the diode based on the received harmonic signals.

24. The method of claim 23 where the first output and the second output from the radio frequency transmitter comprise pulses of different amplitudes.

25. The method of claim 23 where calculating the relationship between the output from the radio frequency transmitter and the current flow in the diode comprises:
computing a first ratio of the first output from the radio frequency transmitter to the first received harmonic signal from the diode;
computing a second ratio of the second output from the radio frequency transmitter to the second received harmonic signal from the diode; and using the difference between the first ratio and the second ratio to determine the amount of current flow in the diode for a range of outputs from the radio transmitter.

* * * * *

UNITED STATES PATENT AND TRADEMARK OFFICE
CERTIFICATE OF CORRECTION

PATENT NO. : 8,725,270 B2  Page 1 of 1
APPLICATION NO. : 13/703288
DATED : May 13, 2014
INVENTOR(S) : Bruce C. Towe It is certified that error appears in the above-identified patent and that said Letters Patent is hereby corrected as shown below:

Title Page, Item (73) Assignee, line 1:

Delete "Arizona Board of Regents," and insert -- The Arizona Board of Regents for and on Behalf of Arizona State University, --.

Signed and Sealed this
Fifth Day of August, 2014

Michelle K. Lee
*Deputy Director of the United States Patent and Trademark Office*